United States Patent
Richardson et al.

[11] Patent Number: 5,524,294
[45] Date of Patent: * Jun. 11, 1996

[54] TAMPER- OR DAMAGE-INDICATING MEMBERS

[76] Inventors: Margaret P. Richardson; Philip Richardson, both of Lluest, Cynwyl Elfed, Carmarthen, United Kingdom, SA33 6TL

[ * ] Notice: The term of this patent shall not extend beyond the expiration date of Pat. No. 5,224,221.

[21] Appl. No.: 83,634

[22] Filed: Jun. 28, 1993

Related U.S. Application Data

[63] Continuation-in-part of Ser. No. 678,307, Apr. 22, 1991, Pat. No. 5,224,221.

[30] Foreign Application Priority Data

Sep. 19, 1988 [GB] United Kingdom .................. 8821957
Feb. 16, 1989 [GB] United Kingdom .................. 8903548

[51] Int. Cl.⁶ ............................................. A41D 13/10
[52] U.S. Cl. .............................. 2/161.7; 2/168; 428/69; 428/916; 206/807
[58] Field of Search ........................... 2/168, 167, 161.7, 2/163, 164, 901, 169, 159, 158, 16, 21, 161.6; 428/69, 916; 128/917, 918, 842, 844; 604/349, 353; 116/264, 266, 270; 206/524.8, 807

[56] References Cited

U.S. PATENT DOCUMENTS

| | | | |
|---|---|---|---|
| 732,360 | 6/1903 | Lindsay | 2/168 |
| 3,110,035 | 11/1963 | Lathe | 2/168 |
| 3,633,216 | 1/1972 | Schonholtz | 2/168 |
| 3,852,826 | 12/1974 | Schindler | 2/168 |
| 4,295,566 | 10/1981 | Vincek | 116/266 |
| 4,516,679 | 5/1985 | Simpson et al. | 206/459 |
| 4,696,065 | 9/1987 | Elenteny | 2/168 |
| 4,742,578 | 5/1988 | Seid | 2/168 |
| 4,755,405 | 7/1988 | Massucco et al. | 428/35 |
| 4,757,557 | 7/1988 | Hirano | 2/168 |
| 4,813,541 | 3/1989 | Velasco et al. | 206/459 |
| 4,816,305 | 3/1989 | Stillwell et al. | 428/35.7 |
| 4,843,014 | 6/1989 | Cukier | 436/36 |
| 4,847,918 | 7/1989 | Sturm | 2/161 R |
| 4,877,143 | 10/1989 | Travisano | 116/270 |
| 4,881,277 | 11/1989 | Hogle | 2/169 |
| 5,017,427 | 5/1991 | Machida et al. | 2/168 |
| 5,317,760 | 6/1994 | Best | 2/161.7 |

Primary Examiner—Amy B. Vanatta
Attorney, Agent, or Firm—Kohn & Associates

[57] ABSTRACT

A apparatus for providing a tamper- or damage-indicating member, such as a tamper-evident glove. The apparatus comprises first and second layers, typically inner and outer glove-shaped bodies, of substantially liquid- and air-impermeable material, at least a portion of the second layer being of translucent material and having a contrasting color relative to the first layer. The apparatus further comprises means for sealing at least the portion of the second layer to the first layer, such that the portion surrounds a zone of the surface of the first layer, forming a space between the layers which is adjacent the zone and is substantially free of air. When the second layer is sealed to the first layer, breach in either layer adjacent the zone results in a change in perceived color in the area of breach.

17 Claims, 1 Drawing Sheet

5,524,294

TAMPER- OR DAMAGE-INDICATING MEMBERS

This is a continuation-in-part of application Ser. No. 07/678,307 filed on Apr. 22, 1991, now U.S. Pat. No. 5,224,221.

FIELD OF THE INVENTION

The present invention is concerned with tamper- or damage-indicating members, and methods of detecting breach of such members.

BACKGROUND OF THE INVENTION

There are many types of article for which it is desirable to provide a visual indication that it has been breached, which may in some circumstances be indicative of accidental damage to the article, and in other circumstances indicative of tampering with the article.

An example of an article for which it is desired to provide a visual indication of accidental damage is a protective glove. Protective gloves are worn by surgeons in the course of surgical operations and are increasingly worn by other medical personnel (such as nurses, dentists and ambulance operatives), as well as other emergency workers, in view of concern over cross-infection in connection with diseases such as hepatitis B and acquired immune deficiency syndrome (AIDS).

The basic rationale behind the use of such gloves is that they should provide a complete barrier between the medical or emergency worker and the patient. Unfortunately, there is a risk of damage to the gloves by the use of sharp instruments such as scalpels, needles and the like; such damage is not always immediately detectable.

Examples of articles where it is desired to provide a visual indication of accidental damage or tampering include containers (particularly containers which are intended to provide security for the contents), coin-meters, seals on lorries and other vehicles, and the like. For such products it is often desirable to provide a visual indication of when a seal has been broken.

It is an object of the invention to provide tamper- or damage-indicating members, and methods for detecting breach (either accidental or as a result of unauthorised tampering) of such members.

SUMMARY OF THE PRESENT INVENTION

There is provided by the present invention a tamper- or damage-indicating member, which comprises an inner layer and an outer layer, at least a portion of the outer layer being sealed to the inner layer so as to surround a zone of the surface of the inner layer which is not sealed to the outer layer, thereby forming a space between the inner and outer layers which is adjacent the above-mentioned zone and is substantially free of air (for example, substantially evacuated), both the outer and inner layers being of substantially liquid- and air-impermeable material at least in the area thereof overlying the latter zone and having a contrasting color relative to the color of the inner layer, such that when there is a breach in either layer adjacent the above-mentioned zone there is a change in perceived color in the area of breach.

It is preferred that in the above-mentioned zone, both the outer and the inner layer should be of substantially uniform coloration throughout. Typically, the outer layer may be of yellow translucent material and the inner layer of a darker color, such as green, black or the like. Because of the optical properties of the outer layer, the perceived color is that of the inner layer when there is a complete vacuum in the above-mentioned zone (when the member is undamaged or not tampered with), the outer layer appearing to be transparent. When the vacuum has been broken, the perceived color will be that of the outer layer (which will then be translucent). When the space is substantially free of air but not fully evacuated (for example, when the outer layer is secured to the inner layer only by the resilience of the outer layer, as will be described in more detail below), the optical effect is reversed. That is, the perceived color when the member is undamaged or not tampered with is that of the outer layer, but when damage has taken place, and in the presence of an aqueous liquid, a capillary action takes place between the two layers such that the perceived color is that of the inner layer.

In some embodiments of the invention, the outer layer is thinner than, or of substantially the same thickness as, the inner layer; the contacting surfaces of the inner and outer layers may both be smooth or, in some embodiments (such as when the outer layer and the inner layer are both flexible), the outer surface of the inner layer, or the inner surface of the outer layer, may have a fine textured finish. In other embodiments (such as when the outer layer and inner layer are both rigid), it is preferred that both the outer surface of the inner layer and the inner surface of the outer layer should be smooth. It is sometimes desirable to provide a release layer between the outer surface of the inner layer and the inner surface of the outer layer. Such a release layer generally minimises the two layers sticking together.

There is still further provided by the present invention an apparatus for providing a tamper- or damage-indicating member, which apparatus comprises:

(a) first and second layers of substantially liquid- and air-impermeable material, at least a portion of the second layer being of translucent material and having a contrasting color relative to the first layer;

(b) means for sealing at least the portion of the second layer to said first layer, such that the above-mentioned portion surrounds a zone of the surface of the first layer, thereby forming a space between the layers which is adjacent the above-mentioned zone and is substantially free of air;

whereby when the second layer is sealed to the first layer as described above, breach in either layer adjacent the above-mentioned zone results in a change in perceived color in the area of breach.

The first and second layers are substantially as hereinbefore described, with reference respectively to the inner and outer layers of the tamper- or damage-indicating member.

There is still further provided by the present invention a method of detecting breach of a tamper- or damage-indicating member, which method comprises:

(a) providing an inner layer of substantially liquid- and air-impermeable material;

(b) providing an outer layer of substantially liquid- and air-impermeable material, at least a portion of the outer layer surrounding a zone of the surface of the inner layer, which zone is not sealed to the outer layer, the outer layer being of translucent material at least in the area thereof overlying the zone and having a contrasting color relative to the color of the inner layer;

(c) sealing the portion of the outer layer to the inner layer so as to form a space between the layers which is adjacent the zone and is substantially free of air; and (d) detecting breach in either layer adjacent the above-mentioned zone by monitoring a change in perceived color in the area of breach.

The sealing typically involves the use of suitable adhesives, welding, or other suitable sealing technique.

In one embodiment of the invention, the tamper- or damage-indicating member is a glove, comprising an inner glove-shaped body and an outer glove-shaped body surrounding the inner body, the inner and outer bodies each being of flexible, liquid- and air-impermeable material, and being sealed together at or near the wrist-engaging edges thereof, a substantial proportion of the outer surface of the inner body being in contact with the inner surface of the outer body but substantially unbonded (that is, not sealed) thereto and the space between the layers being substantially evacuated. In this embodiment of the invention, the outer body is preferably wholly of translucent material. The inner body may be strongly colored, for example, of black, luminous yellow or green.

In the case where the member according to the invention is a glove, in addition to a visible change being detected when the outer layer is damaged, there is sometimes a tactile change, detected by the wearer as the outer layer slides relative to the inner layer.

In an embodiment of the invention in which the tamper- or damage-indicating member is a glove, the inner and outer layers are not bonded to one another but only secured to one another by the resilience of the outer layer. In this embodiment, when the outer layer is breached as a result of tampering or accidental damage, and in the presence of an aqueous liquid, the perceived color is that of the inner layer, as a result of capillary action of the aqueous liquid.

According to this embodiment of the invention, therefore, there is provided a glove having a plurality of layers, the glove comprising an inner glove-shaped body and an outer glove-shaped body surrounding the inner body, the outer body being secured to the inner body by the resilience of the outer body when the glove is worn, the inner and outer bodies each being of flexible, substantially liquid- and air-impermeable material (such as an elastomer), the outer body being translucent and having a contrasting color relative to the color of the inner body, such that when the outer body is breached, and in the presence of an aqueous liquid, there is a change in perceived color in the area of breach as a result of capillary action of the liquid between the bodies.

According to a further aspect of the present invention, there is provided an apparatus effective for providing a tamper-evident glove-shaped member, which apparatus comprises:

(a) a first glove-shaped body; and (b) a second glove-shaped body of translucent material and having a contrasting color relative to the color of the first body;

the bodies each being of flexible, substantially liquid- and air-impermeable material; the second body being configured to surround the first body and be secured thereto by the resilience of the second body when fine bodies are donned by a wearer, such that when the second body is breached, and in the presence of an aqueous liquid, there is a change in perceived color in the area of breach as a result of capillary action of the liquid between the bodies.

There is still further provided by the present invention, a method of providing an apparatus effective for providing a tamper-evident glove-shaped member, which method comprises:

(a) providing a first glove-shaped body having a dark color (preferably dark green); and (b) providing a second glove-shaped body of translucent material and having a contrasting color relative to the color of said first body;

the bodies each being of flexible, substantially liquid- and air-impermeable material; the second body capable of surrounding the first body and being secured thereto by the resilience of the second body when the bodies are donned on a wearer's hand, such that when the second body is breached, and in the presence of an aqueous liquid, there is a change in perceived color in the area of breach as a result of capillary action of the liquid between the bodies.

According to a further aspect of the present invention there is provided a method of monitoring breach of a glove-shaped member, which method comprises:

(a) providing a first glove-shaped body;

(b) providing a second glove-shaped body surrounding the first body and secured thereto by the resilience of the second body, both bodies being worn on a user's hand, the second body being of translucent material and having a contrasting color relative to the color of the first body; the first and second bodies each being of flexible substantially liquid- and air-impermeable material;

(c) allowing an aqueous liquid to penetrate a breach in the second body; and (d) monitoring a perceived color change in the area of breach.

In this embodiment of the invention, a glove may be formed by:

(a) dip forming an elastomeric latex on a hand-shaped former to form a first glove-shaped uncured body;

(b) surface halogenating (e.g. chlorinating) at least part of the dip-formed elastomeric material present on the former;

(c) dip-forming a further elastomeric latex onto the halogenated glove-shaped body to form a further uncured body surrounding the halogenated body; and (d) removing the two bodies jointly from the former, the elastomeric latices being such that the resulting glove-shaped member has an outer layer of a translucent material with a contrasting color relative to the color of the inner layer.

This latter removal step generally involves eversion of the glove-shaped bodies, such that the first applied halogenated body becomes the outer body and the second applied body becomes the inner body when both have been stripped from the former.

The halogenation is preferably controlled to substantially avoid adhesion in the halogenated area; in order to obtain a glove according to the above-mentioned embodiment of the invention in which the inner and outer layers are secured to one another by the resilience of the outer layer, the first uncured body may be halogenated all over the surface thereof. When the two bodies are then removed jointly from the former, they separate (or delaminate) from one another.

The space between the inner and outer bodies may, in some embodiments, include an anti-bacterial or anti-vital material, such as the material commercially available under the trade mark Nonoxynol 9.

For some applications, more than two glove-shaped bodies may be provided, one inside the other; these bodies may be sealed together at or near the wrist-engaging edges thereof. Alternatively, the outer body of such a multi-layer construction may be secured by its inherent resilience, as described above with reference to a two-layer construction.

DETAILED DESCRIPTION OF THE DRAWINGS

Embodiments of the invention will now be described by way of example with reference to the accompanying drawings, wherein FIG. 1 is a scrap-section greatly at enlarged scale through part of a glove according to the invention;

Figure 1:
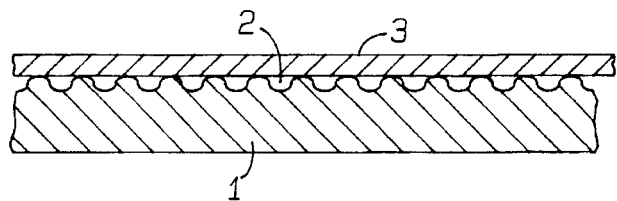

Referring to FIG. 1, an inner glove 1 is of a thin flexible, elastic material (e.g. rubber) or a plastics material, which may be highly colored, for example, of black, luminous yellow, or green. The outer surface 2 of inner glove 1 may be smooth or (as in the illustrated embodiment) may have a fine textured finish. An outer (translucent) glove 3 of contrasting color relative to the inner glove is of the same shape and size as the inner glove and is a close fit thereon. At or near the edges of the gloves 1, 3 which engage the wearer's wrist, the gloves 1, 3 may be sealed together. The space between the gloves 1, 3 is substantially evacuated of air, so that the adjacent surfaces of the gloves 1, 3 are pressed firmly together and the inner and outer gloves 1, 3 act as a single glove.

However, if a small puncture or leak is made in either of the gloves 1, 3 in the presence of aqueous liquids such as blood or body fluids, a color change in the vicinity of the puncture becomes apparent, indicating the existence of the puncture or leak. At the same time, the outer glove 3 becomes relatively more mobile over the inner glove 1 in the vicinity of the puncture, causing a detectable change of feel of the glove.

An appropriate anti-bacterial or anti-viral substance may be dispersed in the space between the gloves 1, 3 to act against any viral material which penetrates into the space.

For some applications, more than two gloves 1, 3 may be provided, one inside the other, all sealed together at the wrist-engaging edges and having the spaces between the gloves air-free.

Figure 2:
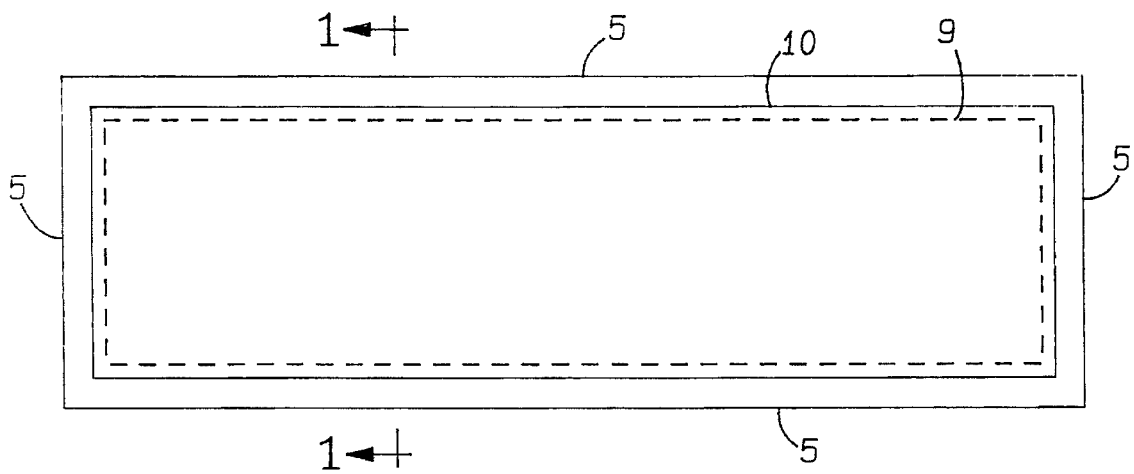
FIG. 2 is a plan view of a portion of a security seal tape according to the invention.
Figure 3:
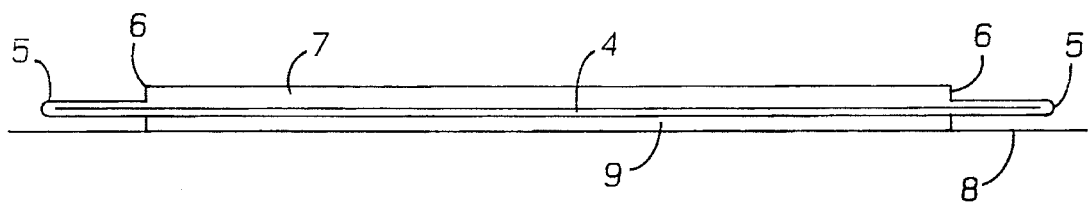
FIG. 3 is a cross-sectional view along line A—A of FIG. 2, with the tape in an undamaged state.
Figure 4:
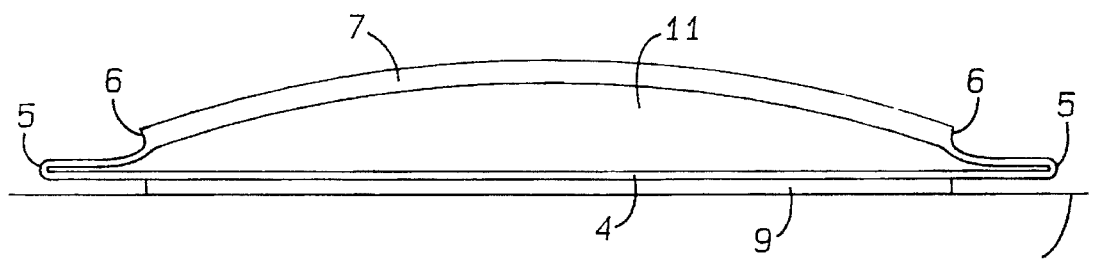
FIG. 4 is a cross-sectional view corresponding to that of FIG. 3 with the tape in a damaged state.

In the embodiment of FIGS. 2 and 3, the undamaged tape member comprising a bottom layer 4 made of deep colored plastics is folded at its edges 5 and welded, or otherwise connected at 6, to the top layer 7 of semi-rigid light-colored translucent plastics, preformed into a shallow trough. The top and bottom layers (7 and 4 respectively) are held together in the undamaged state by a vacuum between the two layers, which are sealed on all four edges, as shown in FIG. 2. The tape member is adhered to a surface 8 using a layer of suitable adhesive 9, applied around a peripheral region 10 (see FIG. 2) which is stronger than the tape itself. This is necessary in order to ensure that the tape cannot be removed from the surface without itself becoming damaged. In FIG. 4, the semi-rigid, preformed top layer 7 has delaminated upon loss of vacuum due to damage of the tape, allowing air to ingress into the region 11. This effect causes the perceived color of the tape member to change, thereby giving a visual indication of damage. It is important to note that the adhesive line 9 is kept back from the folded edge to allow movement of the top layer 7 upon delamination.

Such a security seal may be useful on envelopes or other packages, for cargo vehicles such as lorries and for utility meters such as gas or electricity meters, providing visual assurance that contents have not been tampered with.

While the invention has been primarily described in terms of gloves and security seals, members according to the invention may be used liar other purposes; for example, they may be used in tamper-proof seals tier screw caps (for bottles, jars or the like), such that a visual indication is readily given when the bottle or jar has been opened. Alternatively, the member may be used on the lid of a rip-top can or similar container. In further embodiments, the member according to the invention may be used on consumer goods (e.g. electronic goods) to provide an indication that unauthorised repairs have been carried out.

What we claim is:

1. An apparatus for providing a tamper- or damage-indicating member, which apparatus comprises:

(a) first and second layers of substantially liquid- and air-impermeable material, at least a portion of said second layer being of translucent material and having a contrasting color relative to said first layer;

(b) means for sealing at least said portion of said second layer to said first layer, such that said portion surrounds a zone of the surface of said first layer, thereby forming a space between said layers which is adjacent said zone and is substantially free of air;

whereby, when said second layer is sealed to said first layer, breach in either layer adjacent said zone results in a change in perceived color in the area of breach.

2. An apparatus according to claim 1, wherein at least said portion of said second layer is substantially lighter in color than said zone of said first layer.

3. An apparatus according to claim 1, wherein said second layer is thinner than said first layer.

4. An apparatus according to claim 1 wherein a release layer is provided for arrangement between facing surfaces of said layers.

5. An apparatus according to claim 1, wherein said second layer is wholly of translucent material.

6. An apparatus according to claim 1, wherein said first layer comprises an inner glove-shaped body, and said second layer comprises an outer glove-shaped body capable of surrounding the inner body, said bodies capable of being sealed together at or near the wrist-engaging edges thereof, a substantial proportion of the outer surface of the inner body being in contact with the inner surface of the outer body but substantially unbonded thereto and the space between the layers being substantially evacuated.

7. A apparatus according to claim 6, wherein said bodies are secured to one another by the resilience of the outer body.

8. A method of detecting breach of a tamper- or damage-indicating member, which method comprises:

(a) providing an inner layer of substantially liquid- and air-impermeable material;

(b) providing an outer layer of substantially liquid- and air-impermeable material, at least a portion of said outer layer surrounding a zone off the surface of said inner layer, which zone is not sealed to said outer layer, said outer layer being of translucent material at least in the area thereof overlying said zone and having a contrasting color relative to the color of said inner layer;

(c) sealing said portion of said outer layer to said inner layer so as to form a space between said layers which is adjacent said zone and is substantially free of air; and (d) detecting breach in either layer adjacent said zone by monitoring a change in perceived color in the area of breach.

9. An apparatus effective for providing a tamper-evident glove-shaped member, which apparatus comprises:

(a) a first glove-shaped body; and (b) a second glove-shaped body of translucent material and having a contrasting color relative to the color of said first body:

said bodies each being of flexible, substantially liquid- and air-impermeable material; said second body being configured to surround said first body and be secured thereto by the resilience of said second body when said bodies are donned by a wearer, such that when said second body is breached, and in the presence of an aqueous liquid, there is a change in perceived color in the area of breach as a result of capillary action of said liquid between said bodies.

10. An apparatus according to claim 9, wherein said second body is substantially lighter in color than said first body.

11. An apparatus according to claim 9, wherein said second body is thinner than said first body.

12. An apparatus according to claim 9, wherein a release layer is provided for arrangement between facing surfaces of said bodies.

13. An apparatus according to claim 9, wherein said second body is wholly of translucent material.

14. A method of providing an apparatus effective for providing a tamper-evident glove-shaped member, which method comprises:

(a) providing a first glove-shaped body having a relatively dark color; and (b) providing a second glove-shaped body of translucent material and having a contrasting color relative to the color of said first body;

said bodies each being of flexible, substantially liquid- and air-impermeable material; said second body being capable of surrounding said first body so as to be secured thereto by the resilience of said second body when said bodies are donned on a wearer's hand, such that when said second body is breached, and in the presence of an aqueous liquid, there is a change in perceived color in the area of breach as a result of capillary action of said liquid between said bodies.

15. A method of monitoring breach of a glove-shaped member, which method comprises:

(a) providing a first glove-shaped body;

(b) providing a second glove shaped body surrounding said first body and secured thereto by the resilience of said second body, both bodies being worn on a user's hand, said second body being of translucent material and having a contrasting color relative to the color of said first body; said bodies being of flexible substantially liquid- and air-impermeable material;

(c) allowing an aqueous liquid to penetrate a breach in said second body; and (d) monitoring a perceived color change in the area of breach.

16. A method according to claim 15, wherein said aqueous liquid comprises a body fluid.

17. A method according to claim 15, wherein penetration of said liquid involves capillary action between said bodies, such that the perceived color is that of said first body.

* * * * *